(12) United States Patent
Bryan et al.

(10) Patent No.: US 7,331,963 B2
(45) Date of Patent: Feb. 19, 2008

(54) DRILL HEAD FOR USE IN PLACING AN INTERVERTEBRAL DISC DEVICE

(75) Inventors: Vincent Bryan, Mercer Island, WA (US); Alex Kunzler, Bellevue, WA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 08/944,234

(22) Filed: Oct. 6, 1997

(65) Prior Publication Data

US 2002/0151901 A1 Oct. 17, 2002

(51) Int. Cl.
*A61B 17/00* (2006.01)

(52) U.S. Cl. ............... 606/80; 623/18; 606/61

(58) Field of Classification Search .......... 606/80, 606/81, 79, 180; 660/80–85, 180, 167, 168–171, 660/60–62, 72–79; 623/16, 17, 18; 433/128, 433/144
See application file for complete search history.

(56) References Cited

U.S. PATENT DOCUMENTS

| | | | | |
|---|---|---|---|---|
| 2,025,779 A | * | 12/1935 | Roelke | ......................... 433/128 |
| 3,937,222 A | | 2/1976 | Banko | |
| 4,197,645 A | * | 4/1980 | Scheicher | ................. 433/128 |
| 4,662,891 A | * | 5/1987 | Noiles | .......................... 623/22 |
| 4,781,072 A | * | 11/1988 | Tschudin | ..................... 74/318 |
| 4,842,578 A | | 6/1989 | Johnson et al. | |
| 5,041,119 A | * | 8/1991 | Frigg et al. | ..................... 606/96 |
| 5,122,134 A | * | 6/1992 | Borzone et al. | ............... 606/80 |
| 5,387,215 A | | 2/1995 | Fisher | |
| 5,489,308 A | * | 2/1996 | Kuslich et al. | .......... 623/17.11 |
| 5,527,316 A | * | 6/1996 | Stone et al. | .................. 606/80 |
| 5,601,556 A | | 2/1997 | Pisharodi | |
| 5,628,748 A | * | 5/1997 | Vicari | .......................... 606/79 |
| 5,743,918 A | | 4/1998 | Calandruccio et al. | |
| 5,800,551 A | | 9/1998 | Williamson et al. | |
| 5,810,827 A | | 9/1998 | Haines et al. | ................. 606/80 |
| 5,853,415 A | | 12/1998 | Bertin et al. | |
| 5,904,687 A | | 5/1999 | Del Rio et al. | |
| 6,080,155 A | * | 6/2000 | Michelson | ..................... 606/61 |
| 6,083,228 A | | 7/2000 | Michelson | |

* cited by examiner

*Primary Examiner*—Lien M. Ngo
(74) *Attorney, Agent, or Firm*—Goodwin Procter LLP

(57) ABSTRACT

A drill head for preparing the bone of two opposing vertebral bodies to accept the concaval-convex shape of an endoprosthesis includes a form cutter having at least one predetermined milling surface, drive means, and a housing. The form cutter has a profile allowing the drill head to fit in the narrow space between two opposing vertebral bodies in the cervical spine of a patient. The drill head is used in a method for preparing the disc space between adjacent vertebrae of a human spine to receive an endoprosthesis therebetween, the method being performed by contacting at least one vertebral body with a movable form cutter.

62 Claims, 3 Drawing Sheets

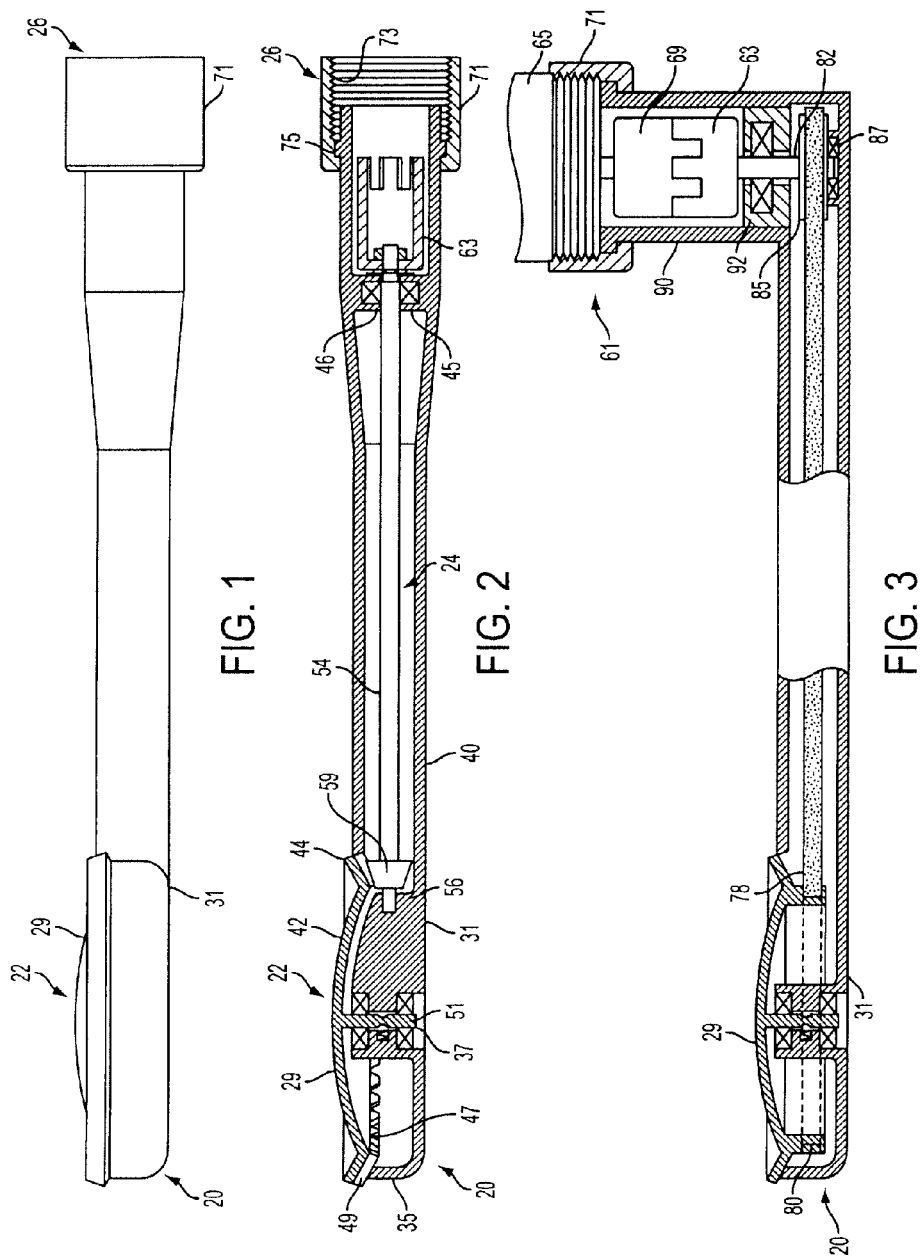

DRILL HEAD FOR USE IN PLACING AN INTERVERTEBRAL DISC DEVICE

BACKGROUND OF THE INVENTION

This invention relates generally to drill heads and more particularly to drill heads for use in placing a vertebral body disc device.

The herniation of a spinal disc and the often resultant symptoms of intractable pain, weakness, sensory loss, incontinence and progressive arthritis are among the most common of debilitating processes affecting mankind. If a patient's condition does not improve after conservative treatment, and if clear physical evidence of nerve root or spinal cord compression is apparent, and if correlating radiographic studies (i.e., MRI or CT imaging or myelography) confirm the condition, surgical removal of the herniated disc may be indicated. The process of discectomy—as the name implies—involves the simple removal of the disc without attempt to replace or repair the malfunctioning unit. In the United States in 1985, over 250,000 such operations were performed in the lumbar spine and in the cervical spine.

Statistics suggest that present surgical techniques are likely to result in short-term relief, but will not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson (Robinson, R. A.: The Results of Anterior Interbody Fusion of the Cervical Spine, J. Bone Joint Surg., 440A: 1569 1586, 1962) that after surgical fusion, osteophyte (bone spur) reabsorption at the fused segment might take place. However, it has become increasingly apparent that unfused vertebral segments at the levels above and below the fused segment degenerate at accelerated rates as a direct result of this fusion. This has led some surgeons to perform discectomy alone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception. Premature degenerative disc disease at the level above and below the excised disc can and does occur.

Spine surgery occasionally involves fusion of the spine segments. In addition to the problems created by disc herniation, traumatic, malignant, infectious and degenerative syndromes of the spine can be treated by fusion. Other procedures can include bone grafts and heavy duty metallic rods, hooks, plates and screws being appended to the patient's anatomy; often they are rigidly and internally fixed. None provide for a patient's return to near-normal functioning. Though these procedures may solve a short-term problem, they can cause other, longer term, problems.

A number of attempts have been made to solve some of the problems described above by providing a patient with spinal disc prostheses, or artificial discs of one sort or another. For example, Steffee, U.S. Pat. No. 5,031,437, describes a spinal disc prosthesis having upper and lower rigid flat plates and a flat elastomeric core sandwiched between the plates. Frey et al., U.S. Pat. Nos. 4,917,704 and 4,955,908, disclose vertebral prostheses, but the prostheses are described as solid bodies.

U.S. Pat. Nos. 4,911,718 and 5,171,281 disclose resilient disc spacers, but no inter-connective or containing planes or like elements are suggested, and sealing the entire unit is not taught.

U.S. Pat. No. 5,674,296, incorporated herein by reference, provides a vertebral disc endoprosthesis which addresses these shortcomings of the prior art. The endoprosthesis comprises a resilient body formed of a material varying in stiffness from a relatively stiff exterior portion to a relatively supple central portion. A concaval-convex means at least partly surrounds that resilient body so as to retain the resilient body between adjacent vertebral bodies of a patient's spine. If medical considerations so indicate, several disc endoprosthesis can be combined with one or more endoprosthetic vertebral bodies in an entire assembly.

The endoprosthesis has a resilient body formed of one or more materials which may vary in stiffness from a relatively stiff exterior annular gasket portion to a relatively supple central nucleus portion. Concaval-convex elements at least partly surround that nucleus portion so as to retain the nucleus portion and gasket between adjacent vertebral bodies in a patient's spine. Assemblies of endoprosthetic discs, endoprosthetic vertebral bodies, and endoprosthetic longitudinal ligaments may be constructed. To implant this endoprosthesis assembly, information is obtained regarding the size, shape, and nature of a patient's damaged spine. Thereafter; one or more prosthetic vertebral bodies and disc units are constructed in conformity with that information. Finally, the completed and conformed vertebral body and disc assembly is implanted in the patient's spine.

In order to place the above endoprosthesis in a patient's spine, the bone of the two opposing vertebral bodies must be prepared in such a manner so as to accept the concaval-convex shape of endoprosthesis. However, currently available drill heads are not always capable of being fit into the narrow space between two opposing vertebral bodies. Further, the narrow space between two opposing vertebral bodies cannot always be expanded to allow admittance of currently available drill heads.

Thus, it is an object of the instant invention to provide a drill head which can fit within the narrow space between two opposing vertebral bodies.

It is another object of the instant invention to provide a drill head which can prepare the bone of the two opposing vertebral bodies to accept the concaval-convex shape of an endoprosthesis.

These and other objects and advantages of the instant invention will be apparent from the following description and drawings.

SUMMARY OF THE INVENTION

The instant invention overcomes the deficiencies of the prior art devices by providing a drill head with a narrow profile which can fit in the space between two opposing vertebral bodies.

The drill head of the instant invention is provided with a form cutter having a convex shape so as to prepare the bone of vertebral bodies to accept the concaval-convex shape of an endoprosthesis.

BRIEF DESCRIPTION OF THE DRAWINGS

FIG. 1 is a side view of one embodiment of the instant invention.

FIG. 2 is a cross-sectional view of the embodiment of FIG. 1.

FIG. 3 is a partial cross-sectional view of an alternate embodiment of the instant invention.

DETAILED DESCRIPTION OF THE INVENTION

Figure 4:
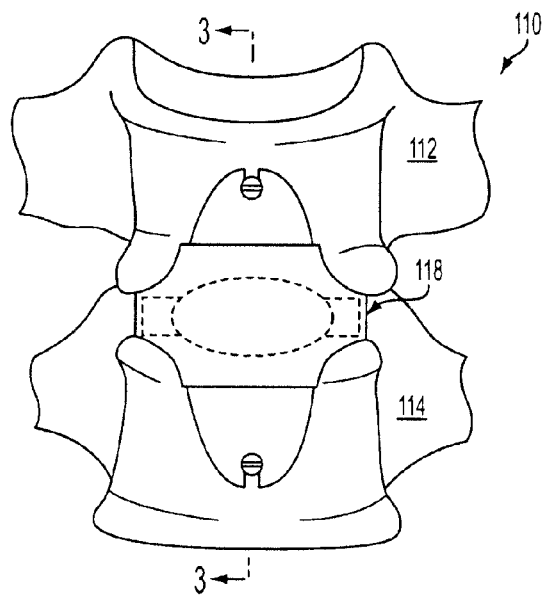
FIG. 4 is a fragmentary vertical view of a portion of a human spine in which is installed a vertebral disc endoprosthesis.

While the invention will be described in connection with a preferred embodiment and procedure, it will be understood that it is not intended to limit the invention to this embodiment or procedure. On the contrary, it is intended to cover all alternatives, modifications, and equivalents as may be included within the spirit and scope of the invention as defined by the appended claims.

One embodiment of the drill head of the present invention is depicted in FIGS. 1 and 2. The drill head 20 generally comprises a form cutter portion 22, drive means 24, and attachment means 26. In accordance with the invention, the form cutter profile imparts a shape to the bone of the vertebral bodies which mates with the predetermined endoprosthesis surface shape.

As seen in FIG. 2, the drill head 20 includes a form cutter 29 carried by a housing 31 having an upstanding wall 35 and a shaft support 37 for supporting the form cutter 29. The housing 31 further includes an elongated shaft portion 40 which houses the drive shaft discussed below. To provide a drill head which can prepare the bone of the two opposing vertebral bodies to accept the concaval-convex shape of an endoprosthesis, the illustrated form cutter 29 has a convex milling surface 42. This convex surface 42 of the form cutter 29 functions to provide the bone of a vertebral body with a mating shape complementary to the concaval-convex shape of the endoprosthesis which is the subject of U.S. Pat. No. 5,674,296.

The form cutter 29 further includes an outwardly and upwardly extending edge 44 about its perimeter. In addition, the undersurface 47 of the form cutter 29 may be provided with a beveled gearing surface 49. Alternately, the beveled gearing surface 49 may be provided about the undersurface of the upstanding edge.

The form cutter 29 is provided with a shaft 51 extending perpendicularly from its undersurface. The form cutter 29 is supported within the housing 31 by the cooperation between the shaft 51 and the shaft support 37. This arrangement permits the form cutter 29 to be removed from the housing 31 by separating the shaft 51 from the shaft support 37. Thus, when the cutter dulls, it can be replaced with a new cutter to ensure accurate and effective performance of the drill head.

In order to provide a drill head which can fit within the narrow space between two opposing vertebral bodies in accordance with the invention, the maximum height of the illustrated form of the cutter portion 22 of the drill head 20 is nine millimeters, Providing the bevel gearing surface 49 on the form cutter 29 allows the drill head 20 to be manufactured with such a narrow profile. This arrangement eliminates the need for a separate gear and form cutter which would likely add to the height of the drill head. Because of its profile, the drill head 20 of the present invention can fit in the narrow space between two opposing vertebral bodies in the cervical spine of a patient.

To provide a driving force to the form cutter 29, the drill head 20 is provided with drive means 24. As shown in FIG. 2, the drive means 24 comprises a drive shaft 54 operatively coupled at its distal end to the form cutter 29 and at its proximal end to a drive source 61. The distal end of the drive shaft 54 is supported by a journal 56 within the housing and is provided with a pinion gear 59. As mentioned above, the undersurface 47 of the form cutter 29 is provided with a beveled gearing surface 49. When the drive shaft 54 rotates, the pinion gear 59 also rotates and cooperates with the beveled gearing surface 49 of the form cutter 29, thereby causing the form cutter 29 to rotate about the shaft 51.

The proximal end of the drive shaft 54 is operatively coupled to a suitable drive source 61 by coupling means 63. Although a drive source is not shown in the embodiment of FIGS. 1 and 2, it should be understood that the drive source shown by FIG. 3 or its functional equivalent could be employed. The illustrated drive source 61 comprises a suitable motor 65 having mating coupling means 69. The motor 65 imparts a driving force to the drive shaft 54 via the mating of the coupling means 63, 69. The drive shaft 54 extends through slot 46 provided in a second upstanding wall 45 at the proximal end of shaft 40.

As shown in FIG. 2, the form cutter 29 is not necessarily oriented at a right angle with respect to the drive shaft 54. In the illustrated device, the angle between the support shaft 51 of the form cutter 29 and the drive shaft 54 is approximately 96° to provide a designed orientation to the vertebral bone surface being milled.

The housing 31, which houses the form cutter 29 and the drive shaft 54, is provided at its proximal end with an attachment means 71. The attachment means 71 allows the drive source to be attached to the drill head 20 of the present invention. In the embodiment of FIG. 2, the drive source is attached to the drill head 20 via threads 73. However, alternate equivalent attaching means could be employed to attach the drive source to the drill head 20. The housing 31 is also provided with a ring 75 about its circumference.

An alternate embodiment of the drive means 24 used in the drill head is shown in FIG. 3. Rather than being driven by a gear and pinion mechanism, the drill head 20 is driven by a drive belt 78. To accommodate the belt driving arrangement, the form cutter 29 is provided with a groove 80 about its perimeter rather than being provided with a beveled gearing surface. The groove 80 interacts with the drive belt 78 to provide a driving force to the form cutter 29. This alternate driving arrangement enables the drill head 20 to be manufactured with a narrow profile.

As mentioned above, in this embodiment of the invention, the drive means 24 comprises a drive belt 78 which is operatively coupled to the form cutter 29 at the distal end of the drill head 20. The belt 78 loops around the form cutter 29 within the groove 80. At the proximal end of the drill head 20, a drive shaft 82 is provided which is operatively coupled to a suitable drive source 61. The drive shaft 82 is provided with a pulley 85 about which the belt 78 is looped. At one end, the drive shaft 82 is supported by the housing 31 with suitable means such as a bearing or bushing 87. At its opposite end, the drive shaft 82 is provided with a coupling means 63 for coupling to a suitable drive source 61. When the drive source 61 acts upon the drive shaft 82 and causes it to rotate, the pulley 85 is caused to rotate, thereby driving the belt 78 and causing the form cutter 29 to rotate.

To accommodate the driving means arrangement of this alternate embodiment, the housing 31 is provided with a perpendicular extension 90 at the proximal end of the drill head 20. The extension 90 is provided with the attachment means 71 for attaching the drill head 20 to a suitable drive source 61. It is within the extension 90 that the drive shaft 82 is coupled to the drive source 61. The housing extension 90 is further provided with an intermediate support member 92 for providing additional support to the drive shaft 82.

As mentioned above, the drill head 20 generally comprises a form cutter portion 22, drive means 24, and attachment means 26. In accordance with the invention, the form cutter profile imparts a shape to the bone of the vertebral bodies which mates with the predetermined endoprosthesis surface shape.

As also stated above, as seen in FIG. 2, the drill head 20 includes a form cutter 29 carried by a housing 31 having an upstanding wall 35 and a shaft support 37 for supporting the form cutter 29. The housing 31 further includes an elongated shaft portion 40 which houses the drive shaft discussed below. To provide a drill head which can prepare the bone of the two opposing vertebral bodies to accept the concaval-convex shape of an endoprosthesis, the illustrated form cutter 29 has a convex milling surface 42. This convex surface 42 of the form cutter 29 functions to provide the bone of a vertebral body with a mating shape complementary to the concaval-convex shape of the endoprosthesis which is the subject of U.S. Pat. No. 5,674,296. The form cutter 29 further includes an outwardly and upwardly extending edge 44 about its perimeter.

As further explained above, in order to provide a drill head which can fit within the narrow space between two opposing vertebral bodies in accordance with the invention, the maximum height of the illustrated form of the cutter portion 22 of the drill head 20 is nine millimeters. Because of its profile, the drill head 20 of the present invention can fit in the narrow space between two opposing vertebral bodies in the cervical spine of a patient.

Figures 5, 6:
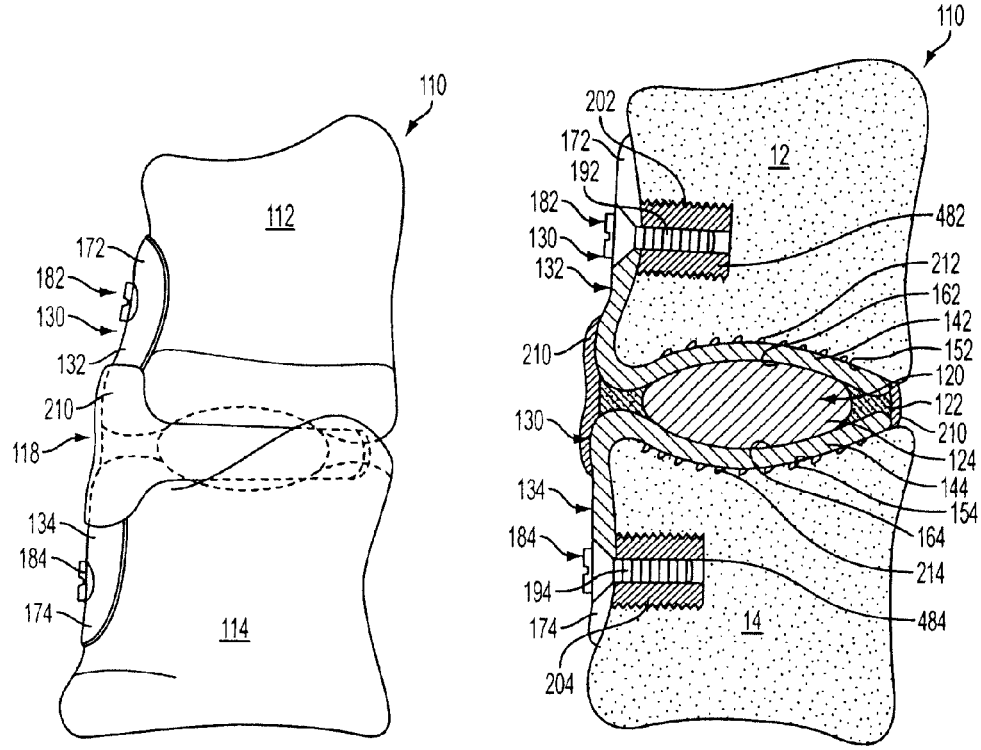
FIG. 5 is a fragmentary side elevational view similar to FIG. 4 showing the elements of a patient's spine and having a vertebral disc endoprosthesis installed therein.
FIG. 6 is a sectional view taken substantially in the plane of line 3-3 in FIG. 4.

Turning more specifically to FIGS. 4-6, a portion of a human spine 110 is shown. The illustrated spine 110 has been subjected to a discectomy surgical process. To discourage degeneration of or damage to the natural vertebral bodies 112 and 114 and their respective facet joints, a vertebral disc endoprosthesis 118 is affixed between the adjacent natural vertebral bodies 112 and 114. This vertebral disc endoprosthesis 118 comprises a resilient disc body 120 having a relatively stiff annular gasket exterior portion 122 and a relatively supple nuclear central portion 124.

In the illustrative vertebral disc endoprosthesis described in detail in U.S. Pat. No. 5,674,296, concaval-convex means 130 surround the resilient body 120 to retain the resilient body 120 between the adjacent natural vertebral bodies 112, 114 in a patient's spine 110. To this end, as shown in FIG. 6, the concaval-convex means 130 comprise two generally L-shaped supports 132 and 134. The supports 132, 134 each have confronting first concaval-convex legs 142, 144, each leg being of relatively constant cross-sectional thickness. Each leg 142, 144 has an outer convex surface 152, 154 for engaging the adjacent bone of the natural vertebral bodies 112, 114. Corresponding inner concave surfaces 162, 164 in confronting array retain the resilient body 120 in its illustrated compressive force shock-absorbing position.

As further described in U.S. Pat. No. 5,674,296, supports 132 and 134 can undergo principle movement away from one another, but only limited secondary translational, rotational and distractional motion will occur. Each support 132, 134 has a second wing or leg 172, 174 extending generally perpendicularly to the first legs 142, 144 respectively, and adapted for affixation to the adjacent bone structure. This affixation is effectively accomplished by cannulated screw devices 182, 184, each of which comprises a screw 192, 194; and a screw anchor 202, 204 adapted to threadably receive the screw extends radially into and seats within the bone structure 112, 114 as especially shown in FIG. 6.

As also described in U.S. Pat. No. 5,674,296, to discourage and prohibit migration of fluids between the endoprosthesis 118 and adjacent parts of the anatomy, a seal member 210 is attached to the supports 132, 134 so as to surround the resilient body 120 comprised of the gasket 122 and nucleus 124. The seal member 210 comprises a flexible sheet material having a multiplicity of pores. Preferably, the pores are from about 5 microns to about 60 microns in size. Flexible, strong polymer sheet materials from which this seal is formed are described in U.S. Pat. No. 5,674,296. Known sealing material can be applied to the flexible sheet material so as to render the flexible sheet material substantially impervious to the passage of any fluid. A watertight seal is perfected when the seal 210 is glued or otherwise affixed to the legs 142, 144 and mediate portions of the legs 172, 174 as suggested in FIGS. 3-6.

Figure 7:
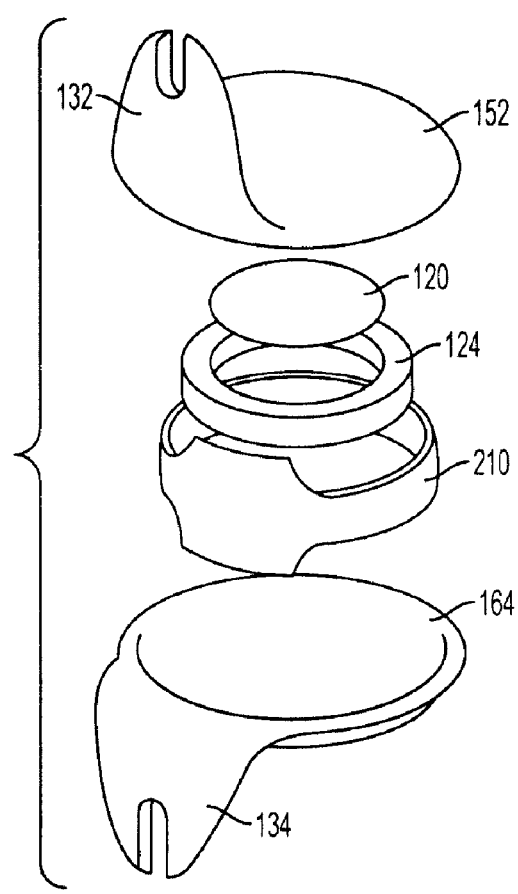
FIG. 7 is an exploded view of the vertebral disc endoprosthesis.

FIG. 7 is an exploded view of a representative vertebral disc endoprosthesis, in which the outer convex surface 152 of concaval-convex means 132 for engaging the adjacent bone of the natural vertebral body and the inner concave surface 164 of concaval-convex means 134 confronting resilient body 120 are shown. In this embodiment of the endoprosthesis 118, the resilient body 120 is surrounded by a gasket 122 and a seal member 210.

As illustrated in FIGS. 4-6, It is necessary to install the endoprosthesis so as to accurately mate the outer convex surface 152, 154 of the endoprosthesis 118 with an adjacent specifically formed bone surface 212, 214 on the ends of vertebrae 112, 114.

To implant the endoprosthesis assembly, information is obtained regarding the size, shape, and nature of a patient's damaged natural spinal discs. If one or more of the patient's vertebral bodies also require replacement, information about those bodies is also obtained. Thereafter, one or more prosthetic disc units are constructed and preassembled in conformity with that information. Finally, the completed and conformed prosthetic disc unit is implanted in the patient's spine.

More specifically, in one embodiment of the method of preparing the disc space between adjacent vertebrae of a human spine to receive an insert therebetween, a surgeon or medical technician develops information about the size, shape and nature of a patient's damaged vertebral body or bodies from radiographs, CT and/or MRI scans, noting specifically the anterior-posterior and lateral dimensions of the end plate of each involved vertebral body and the vertical height of the anterior aspect of each involved vertebral and/or proximate vertebral body and vertical height of the mid portion of involved and proximate relatively normal intervertebral disc spaces. This information is transmitted by telephone, computer datalink or documentary transport to a specialized laboratory. That laboratory constructs one or more prosthetic assemblies including at least one prosthetic disc unit 118 as shown in FIGS. 4-6, which comprises, in turn, the concaval-convex elements 130; the resilient body 120 interposed between the concaval-convex elements; and the seal unit 210 secured around the interior legs and resilient body.

When the unit or units have been received and the patient properly prepared, the damaged natural spinal disc or discs and vertebral body or bodies are removed and the adjacent spinal bone surfaces are milled or otherwise formed to provide concave surfaces 212, 214, to receive the confronting convex surfaces 152, 154.

In order to accurately locate the concaval-convex surfaces in the patient's spine, it is advantageous to precisely locate and form holes 482, 484 (FIG. 6) in the bone structure using a measuring instrument centered in the evacuated natural intravertebral disc space. These holes are then tapped to form female threads therein. When the threads have been formed, the anchors 202, 204 are implanted in the respective tapped holes, thereby creating an imaginary platform of reference points located precisely with respect to the patient's spine.

After the holes have been formed and the anchors 202, 204 implanted, a bone surface milling jig (Not shown) is affixed to the anchors 202, 204 and the desired surfaces of predetermined shape are formed on the interior and superior surfaces of the opposing vertebral bodies using a drill head. The desired surface of predetermined shape 212, 214 is formed by contacting the interior or superior surface of opposing vertebral bodies 112, 114, with a form cutter having at least one milling surface selected a predetermined surface contour in one of the adjacent vertebral bodies as the form cutter is moved by drive means 24, using one of a selection of predetermined form cutter sizes.

Thereafter, the bone milling jig is removed and the concaval-convex elements 152, 154 identical in shape to the milled surfaces 212, 214 are inserted between the distracted milled vertebral bodies 112, 114. The distraction device is then moved. The concaval-convex structures are then attached by the same anchors 202, 204 to the bone, thus insuring a precise and stable mate between the bone surfaces and the convex surfaces 152, 154.

The invention claimed is:

1. A device for preparing a space in a human spine to receive an insert between adjacent vertebral bodies, said device comprising:
    an elongated shaft portion including a drive shaft disposed therein, the drive shaft including a gear at its distal end, whereby the gear is configured to mate with corresponding teeth on the form cutter;
    a housing disposed at the distal end of said elongated shaft portion;
    a drive means;
    a drive source operably connected to said drive means, wherein the drive shaft is rotatably driven by the drive source; and
    a form cutter mountable on said housing and movable by said drive means, wherein:
    said form cutter has at least one top milling surface and bottom milling surface selected to create a surface contour in one of the adjacent vertebral bodies as said form cutter is moved by said drive means, the bottom milling surface is provided with a beveled gearing surface, said beveled gearing surface engages teeth on said gear, and said gear and said beveled gearing surface cooperate to rotate said form cutter as said drive shaft is rotatably driven.

2. The device of claim 1, wherein said housing is fixedly connected to said elongated shaft portion.

3. The device of claim 1, wherein:
    said housing includes a shaft support; and
    said form cutter includes a form cutter shaft configured to fit within said shaft support of said housing.

4. The device of claim 1, wherein said at least one milling surface is configured such that it is operated in a plane generally parallel to the surface contour formed in one of the adjacent vertebral bodies as said form cutter is moved by said drive means.

5. The device of claim 1 including drive means that operatively couples said form cutter to said drive source.

6. The device of claim 5, wherein:
    the drive means comprises a drive shaft having a proximal end and a distal end;
    said drive shaft is adapted to be received in said elongated shaft portion;
    the distal end of said drive shaft is operatively coupled to said form cutter to move said form cutter; and
    the proximal end of said drive shaft is operatively coupled to said drive source.

7. The device of claim 1, wherein said drive means is disposed at least in part in said elongated shaft portion.

8. The device of claim 1, wherein:
    said housing includes a surface formed on a side of said housing opposite said at least one milling surface; and
    said surface is configured to allow a surgeon to increase the pressure of said at least one milling surface against the one of the adjacent vertebral bodies.

9. The device of claim 1, wherein said form cutter includes a leading edge configured as a bone cutting surface.

10. The device of claim 1, wherein at least one of said milling surfaces of said form cutter is convex.

11. The device of claim 1, wherein at least one of said milling surfaces of said form cutter is tapered outwardly from a front surface of said form cutter.

12. A device for preparing a space in a human spine to receive an insert between adjacent vertebral bodies, said device comprising:
    an elongated shaft portion including a drive shaft disposed therein, the drive shaft including a gear at its distal end, whereby the gear is configured to mate with corresponding teeth on the form cutter;
    a housing disposed at the distal end of said elongated shaft portion;
    a drive means;
    a drive source operably connected to said drive means, wherein the drive shaft is rotatably driven by the drive source;
    a form cutter mountable on said housing and movable by said drive means, wherein:
    said form cutter has at least one top milling surface and bottom milling surface selected to create a predetermined surface contour in one of the adjacent vertebral bodies as said form cutter is moved by said drive means, the bottom milling surface is provided with a beveled gearing surface, said beveled gearing surface engages teeth on said gear, and said gear and said beveled gearing surface cooperate to rotate said form cutter as said drive shaft is rotatably driven; and
    said housing has a surface formed on a side of said housing opposite said milling surface.

13. The device of claim 12, wherein said housing is fixedly connected to said elongated shaft portion.

14. The device of claim 12, wherein:
    said housing includes a shaft support; and
    said form cutter includes a form cutter shaft configured to fit within said shaft support of said housing.

15. The device of claim 12, wherein said at least one milling surface is configured such that it is operated in a plane generally parallel to the surface contour formed in one of the adjacent vertebral bodies as said form cutter is moved by said drive means.

16. The device of claim 12 including drive means that operatively couples said form cutter to said drive source.

17. The device of claim 16, wherein:
said drive means comprises a drive shaft having a proximal end and a distal end;
said drive shaft is adapted to be received in said elongated shaft portion;
the distal end of said drive shaft is operatively coupled to said form cutter to move said form cutter; and
the proximal end of said drive shaft is operatively coupled to said drive source.

18. The device of claim 12, wherein said drive means is disposed at least in part in said elongated shaft portion.

19. The device of claim 12, wherein said form cutter includes a leading edge configured as a bone cutting surface.

20. The device of claim 12, wherein at least one of said milling surfaces of said form cutter is convex.

21. The device of claim 12, wherein at least one of said milling surfaces of said form cutter is tapered outwardly from a front surface of said form cutter.

22. A device for preparing a space in a human spine to receive an insert between adjacent vertebral bodies, said device comprising:
an elongated shaft portion including a drive shaft disposed therein, the drive shaft including a gear at its distal end, whereby the gear is configured to mate with corresponding teeth on the form cutter;
a housing disposed at the distal end of said elongated shaft portion;
a drive means;
a drive source operably connected to said drive means, wherein the drive shaft is rotatably driven by the drive source; and
a form cutter mountable on said housing and movable by said drive means, wherein:
said form cutter has at least one top face having first and second milling surfaces selected to create a predetermined surface contour in one of the adjacent vertebral bodies as said form cutter is moved by said drive means, the bottom surface is provided with a beveled gearing surface, said beveled gearing surface engages teeth on said gear, and said gear and said beveled gearing surface cooperate to rotate said form cutter as said drive shaft is rotatably driven.

23. The device of claim 22, wherein said housing is fixedly connected to said elongated shaft portion.

24. The device of claim 22, wherein:
said housing includes a shaft support; and
said form cutter includes a form cutter shaft configured to fit within said shaft support of said housing.

25. The device of claim 22, wherein said top face is configured such that it is operated in a plane generally parallel to the surface contour formed in one of the adjacent vertebral bodies as said form cutter is moved by said drive means.

26. The device of claim 22 including drive means that operatively couples said form cutter to said drive source.

27. The device of claim 26, wherein:
said drive means comprises a drive shaft having a proximal end and a distal end;
said drive shaft is adapted to be received in said elongated shaft portion;
the distal end of said drive shaft is operatively coupled to said form cutter to move said form cutter; and
the proximal end of said drive shaft is operatively coupled to said drive source.

28. The device of claim 22, wherein said drive means is disposed at least in part in said elongated shaft portion.

29. The device of claim 22, wherein said housing includes a surface formed on a side of said housing opposite said top face, said surface being configured to allow a surgeon to increase the pressure of said top face against the one of the adjacent vertebral bodies.

30. A device for preparing a space in a human spine to receive an insert between adjacent vertebral bodies, said device comprising:
an elongated shaft portion;
a housing disposed at the distal end of said elongated shaft portion;
a drive means;
a drive source operably connected to said drive means; and
a form cutter mountable on said housing and movable by said drive means, wherein:
said form cutter has at least one milling surface selected to create a concaval-convex surface contour in one of the adjacent vertebral bodies as said form cutter is moved by said drive means, said form cutter having a beveled gearing surface on the undersurface of the form cutter, wherein said beveled gearing surface cooperates with a pinion gear provided on the distal end of a drive shaft.

31. A device for preparing a space in a human spine to receive an insert between adjacent vertebral bodies, said device comprising:
an elongated shaft portion;
a housing disposed at the distal end of said elongated shaft portion;
a drive shaft;
a drive source operably connected to said drive shaft; and
a form cutter mountable on said housing and movable by said drive shaft, wherein: said form cutter has at least one milling surface selected to create a surface contour in one of the adjacent vertebral bodies as said form cutter is moved by said drive shaft, and an undersurface having a beveled gearing surface which cooperates with a pinion gear on said drive shaft.

32. A device for preparing a space in a human spine to receive an insert between adjacent vertebral bodies, said device comprising:
an elongated shaft portion;
a housing disposed at the distal end of said elongated shaft portion;
a drive shaft;
a drive source operably connected to said drive shaft; and
a form cutter mountable on said housing and movable by said drive shaft, wherein: said form cutter has at least one milling surface selected to create a surface contour in one of the adjacent vertebral bodies as said form cutter is moved by said drive shaft, and an undersurface having a tooth surface which cooperates with a pinion gear on said drive shaft.

33. The device of claim 30, wherein said housing is fixedly connected to said elongated shaft portion.

34. The device of claim 30, wherein:
said housing includes a shaft support; and
said form cutter includes a form cutter shaft configured to fit within said shaft support of said housing.

35. The device of claim 30, wherein said at least one milling surface is configured such that it is operated in a plane generally parallel to the surface contour formed in one of the adjacent vertebral bodies as said form cutter is moved by said drive means.

36. The device of claim 30 including drive means that operatively couples said form cutter to said drive source.

37. The device of claim 36, wherein:
the drive means comprises a drive shaft having a proximal end and a distal end;
said drive shaft is adapted to be received in said elongated shaft portion;
the distal end of said drive shaft is operatively coupled to said form cutter to move said form cutter; and
the proximal end of said drive shaft is operatively coupled to said drive source.

38. The device of claim 30, wherein said drive means is disposed at least in part in said elongated shaft portion.

39. The device of claim 30, wherein:
said housing includes a surface formed on a side of said housing opposite said at least one milling surface; and
said surface is configured to allow a surgeon to increase the pressure of said at least one milling surface against the one of the adjacent vertebral bodies.

40. The device of claim 30, wherein said form cutter includes a leading edge configured as a bone cutting surface.

41. The device of claim 30, wherein at least one of said milling surfaces of said form cutter is convex.

42. The device of claim 30, wherein at least one of said milling surfaces of said form cutter is tapered outwardly from a front surface of said form cutter.

43. The device of claim 31, wherein said housing is fixedly connected to said elongated shaft portion.

44. The device of claim 31, wherein:
said housing includes a shaft support; and
said form cutter includes a form cutter shaft configured to fit within said shaft support of said housing.

45. The device of claim 31, wherein said at least one milling surface is configured such that it is operated in a plane generally parallel to the surface contour formed in one of the adjacent vertebral bodies as said form cutter is moved by said drive means.

46. The device of claim 31 including drive means that operatively couples said form cutter to said drive source.

47. The device of claim 46, wherein:
the drive means comprises a drive shaft having a proximal end and a distal end;
said drive shaft is adapted to be received in said elongated shaft portion;
the distal end of said drive shaft is operatively coupled to said form cutter to move said form cutter; and
the proximal end of said drive shaft is operatively coupled to said drive source.

48. The device of claim 31, wherein said drive means is disposed at least in part in said elongated shaft portion.

49. The device of claim 31, wherein:
said housing includes a surface formed on a side of said housing opposite said at least one milling surface; and
said surface is configured to allow a surgeon to increase the pressure of said at least one milling surface against the one of the adjacent vertebral bodies.

50. The device of claim 31, wherein said form cutter includes a leading edge configured as a bone cutting surface.

51. The device of claim 31, wherein at least one of said milling surfaces of said form cutter is convex.

52. The device of claim 31, wherein at least one of said milling surfaces of said form cutter is tapered outwardly from a front surface of said form cutter.

53. The device of claim 32, wherein said housing is fixedly connected to said elongated shaft portion.

54. The device of claim 32, wherein:
said housing includes a shaft support; and
said form cutter includes a form cutter shaft configured to fit within said shaft support of said housing.

55. The device of claim 32, wherein said at least one milling surface is configured such that it is operated in a plane generally parallel to the surface contour formed in one of the adjacent vertebral bodies as said form cutter is moved by said drive means.

56. The device of claim 32 including drive means that operatively couples said form cutter to said drive source.

57. The device of claim 56, wherein:
the drive means comprises a drive shaft having a proximal end and a distal end;
said drive shaft is adapted to be received in said elongated shaft portion;
the distal end of said drive shaft is operatively coupled to said form cutter to move said form cutter; and
the proximal end of said drive shaft is operatively coupled to said drive source.

58. The device of claim 32, wherein said drive means is disposed at least in part in said elongated shaft portion.

59. The device of claim 32, wherein:
said housing includes a surface formed on a side of said housing opposite said at least one milling surface; and
said surface is configured to allow a surgeon to increase the pressure of said at least one milling surface against the one of the adjacent vertebral bodies.

60. The device of claim 32, wherein said form cutter includes a leading edge configured as a bone cutting surface.

61. The device of claim 32, wherein at least one of said milling surfaces of said form cutter is convex.

62. The device of claim 32, wherein at least one of said milling surfaces of said form cutter is tapered outwardly from a front surface of said form cutter.

* * * * *